(12) United States Patent
Randrianarivo et al.

(10) Patent No.: US 6,630,108 B1
(45) Date of Patent: Oct. 7, 2003

(54) OPTICAL MEASURING HEAD, IN PARTICULAR FOR AUTOMATIC CHEMICAL OR BIOLOGICAL REACTION ANALYZER

(75) Inventors: Jeanet Randrianarivo, Saint Martin de Londres (FR); Christiaan Vermeulen, Crusseilles (FR); Andre Chojnacki, Meylan (FR)

(73) Assignee: Maxmat SA, Montpellier (FR)

( * ) Notice: Subject to any disclaimer, the term of this patent is extended or adjusted under 35 U.S.C. 154(b) by 0 days.

(21) Appl. No.: 09/806,869

(22) PCT Filed: Oct. 4, 1999

(86) PCT No.: PCT/FR99/02360
§ 371 (c)(1),
(2), (4) Date: Apr. 5, 2001

(87) PCT Pub. No.: WO00/22418
PCT Pub. Date: Apr. 20, 2000

(30) Foreign Application Priority Data
Oct. 8, 1998 (FR) .............................. 98 12757

(51) Int. Cl.[7] .............................................. G01N 21/25
(52) U.S. Cl. .................. 422/65; 422/82.08; 422/82.09; 356/73; 356/432
(58) Field of Search ............................. 422/65, 82.08, 422/82.09; 356/73, 432, 440, 434

(56) References Cited

U.S. PATENT DOCUMENTS

| | | | | |
|---|---|---|---|---|
| 3,736,432 A | * | 5/1973 | Sweet .......................... | 377/10 |
| 4,240,751 A | * | 12/1980 | Linnecke et al. ........... | 356/409 |
| 5,169,601 A | * | 12/1992 | Ohta et al. .................... | 422/73 |
| 5,730,941 A | * | 3/1998 | Lefevre et al. ............... | 422/73 |
| 5,892,577 A | * | 4/1999 | Gordon ........................ | 356/73 |
| 6,024,920 A | * | 2/2000 | Cunanan ...................... | 422/65 |

FOREIGN PATENT DOCUMENTS

| | | |
|---|---|---|
| DE | 35 00 639 A1 | 7/1985 |
| DE | 41 17 008 A1 | 11/1991 |
| FR | 2 669 428 | 5/1992 |

* cited by examiner

*Primary Examiner*—Jeffrey Snay
(74) *Attorney, Agent, or Firm*—Oliff & Berridge, PLC.

(57) ABSTRACT

An optical measuring head 10 of an automatic chemical or biochemical reaction analyzer comprises a first calorimetric analysis detector 12 controlled by a light source 20 associated to an optic fibre 28 for transmission of the light beam to one of the sides of a reaction analysis plate 18. A photodetector device 37 is arranged on the opposite side to collect the light beam emerging from the cup 16. The light source 20 and the reaction analysis plate 18 are stationary whereas the measuring head 10 is mounted on a U-shaped mobile support 19 framing the parallel opposite faces of the analysis plate 18 and able to be moved by a drive mechanism 48 facing a predetermined cup 16. The optic fibre 28 has one end secured to the fixed light source 20 and an opposite end arranged in a housing 30 of the mobile support 19.

20 Claims, 4 Drawing Sheets

OPTICAL MEASURING HEAD, IN PARTICULAR FOR AUTOMATIC CHEMICAL OR BIOLOGICAL REACTION ANALYZER

BACKGROUND OF THE INVENTION

The invention relates to an optical measuring head for an automatic laboratory chemical or biochemical reaction analyser designed to determine the dosing of components contained in samples after mixing with reagents in cups of a reaction analysis plate, said measuring head comprising:

a first calorimetric analysis detector controlled by a light source associated to an optic fibre for transmission of the light beam to one of the sides of the reaction analysis plate, coinciding with the optic axis of a predetermined cup, which cup is made of transparent material, means for focussing the light beam when the latter passes through the reaction mixture in said cup, a photodetector device arranged on the opposite side of the analysis plate to collect the light beam emerging from the cup after this beam has been subjected to an attenuation, and an electronic processing circuit for processing the signal delivered by the photodetector device to determine the light spectrum or the optical density of the reaction mixture.

STATE OF THE PRIOR TECHNIQUE

To perform measurement of the optical density of a solid, liquid or gas medium, it is necessary to have a reference light source. This light source operates in conjunction with an optical focussing, collimation or filtering system to generate the incident beam The whole of the measurement chain is mobile and the analysis plate samples are fixed. Vibrations of the filament lamps can however give rise to measurement errors and reduce the lifetime of the lamps.

OBJECT OF THE INVENTION

A first object of the invention is to achieve an improved optical measuring head for a sample analyser by high precision colorimetry.

A second object of the invention is to achieve a multiple optical measuring head suitable for an automatic analyser integrating at least two measuring systems for different applications and enabling the same sample and reagent storage equipment, the same sampling equipment and the same analysis plate to be kept.

The optical measuring head according to the invention is characterized in that:

the light source and the reaction analysis plate are fixed, the measuring head comprises a U-shaped mobile support framing the parallel opposite sides of the reaction analysis plate and a drive mechanism of said mobile support to bring the first colorimetric analysis detector to face a predetermined cup, the optic fibre has one end secured to the fixed light source and an opposite end arranged in a first housing of the mobile support.

The light source and the analysis plate are isolated from the measuring head, and the advantage of the system lies in the fact that the light source and the sample to be analysed are protected from mechanical vibrations. The optic fibre arranged between the fixed light source and the bottom part of the mobile support is alone subjected to torsional and flectional deformation movements during positioning of the measuring head. To prevent premature wear of the optic fibre due to the mechanical frictions caused by deformation, optic fibres provided with an external protective film made of highly resistant material should advantageously be used.

According to a preferred embodiment, the first housing of the mobile support contains an optical collimator to deliver a parallel light beam and a reference photoelectric detector connected to the electronic circuit to compensate the light flux variations when deformation of the optic fibre occurs. A second housing is located opposite the first housing and contains an optical focussing system optically linked with the photo-detector device.

According to one feature of the invention, the optical focussing system of the photo-detector device is connected to a diffraction network for static wavelength selection.

According to a development of the invention, the measuring head is equipped with a second photometric analysis detector arranged on the mobile support to perform an opacimetry measurement. The second photometric analysis detector comprises at least one light-emitting diode for emission of a monochromatic light, operating in conjunction with a receiver photodiode on the opposite side of the mobile support.

It is thus possible to integrate two different reading systems in the measuring head of an analyser, enabling analyses to be performed on the one hand in biochemistry and immunology and on the other hand for hemostatic reactions, using the same sample and reagent storage equipment, the same sampling equipment, and the same analysis plate.

In the analyser using the measuring head according to the invention, the bottom face of the analysis plate is confined in an enclosure kept at a preset temperature by a thermostatic control. The enclosure is advantageously provided with a deformable flexible wall allowing the mobile support to move under the analysis plate.

According to another feature of the invention, the bottom face of the analysis plate is confined in an enclosure kept at a preset temperature by a thermostatic control. The enclosure is advantageously provided with a deformable flexible wall allowing the mobile support to move under the analysis plate.

BRIEF DESCRIPTION OF THE DRAWINGS

Other advantages and features will become more clearly apparent from the following description of an embodiment of the invention given as a non-restrictive example only and represented in the accompanying drawings in which.

DESCRIPTION OF A PREFERRED EMBODIMENT

Figure 1:
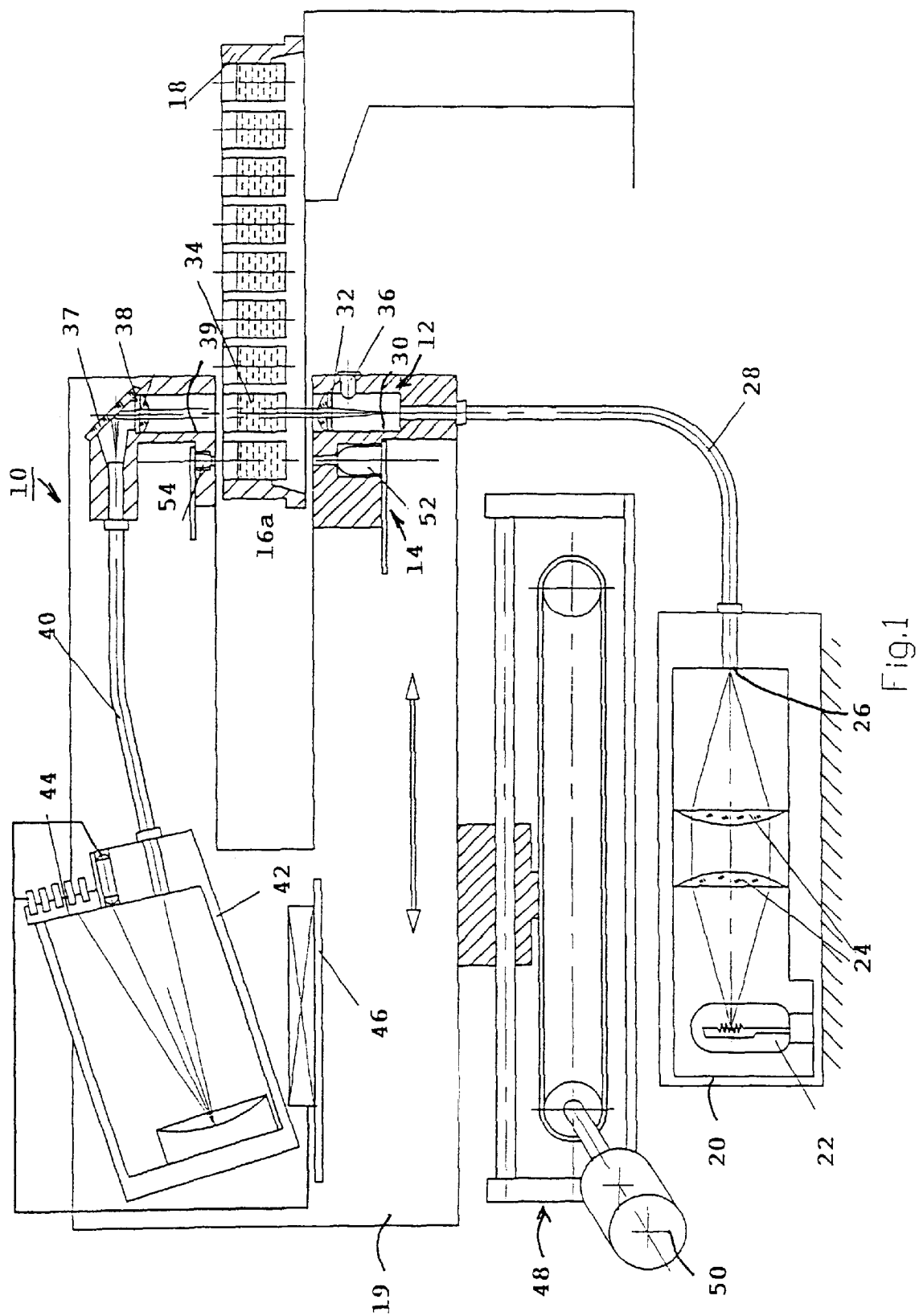
FIG. 1 is a schematic view of the analyser equipped with a mixed measuring head by colorimetry and photometry according to the invention.
Figure 2:
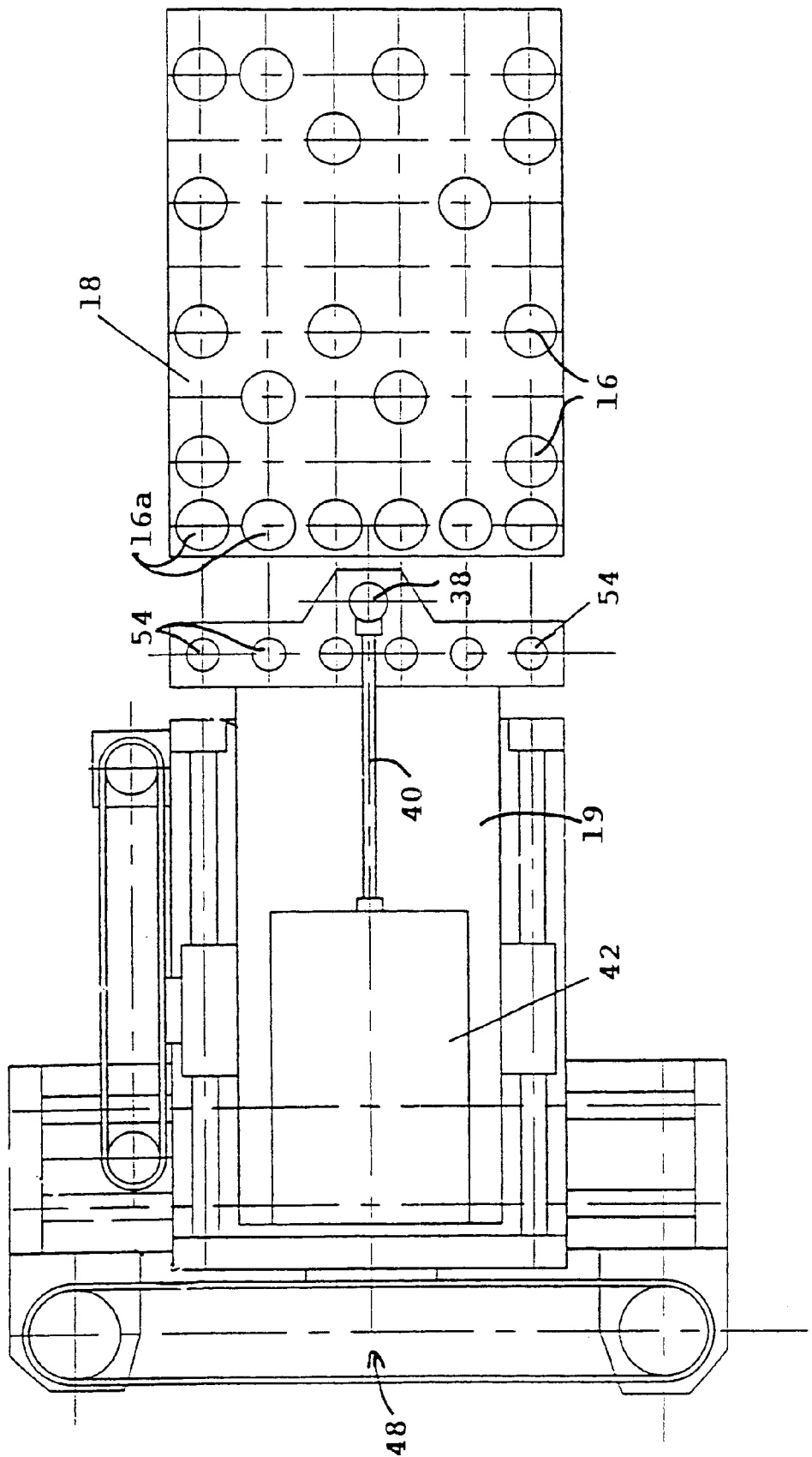
FIG. 2 shows a plan view of FIG. 1.
Figure 3:
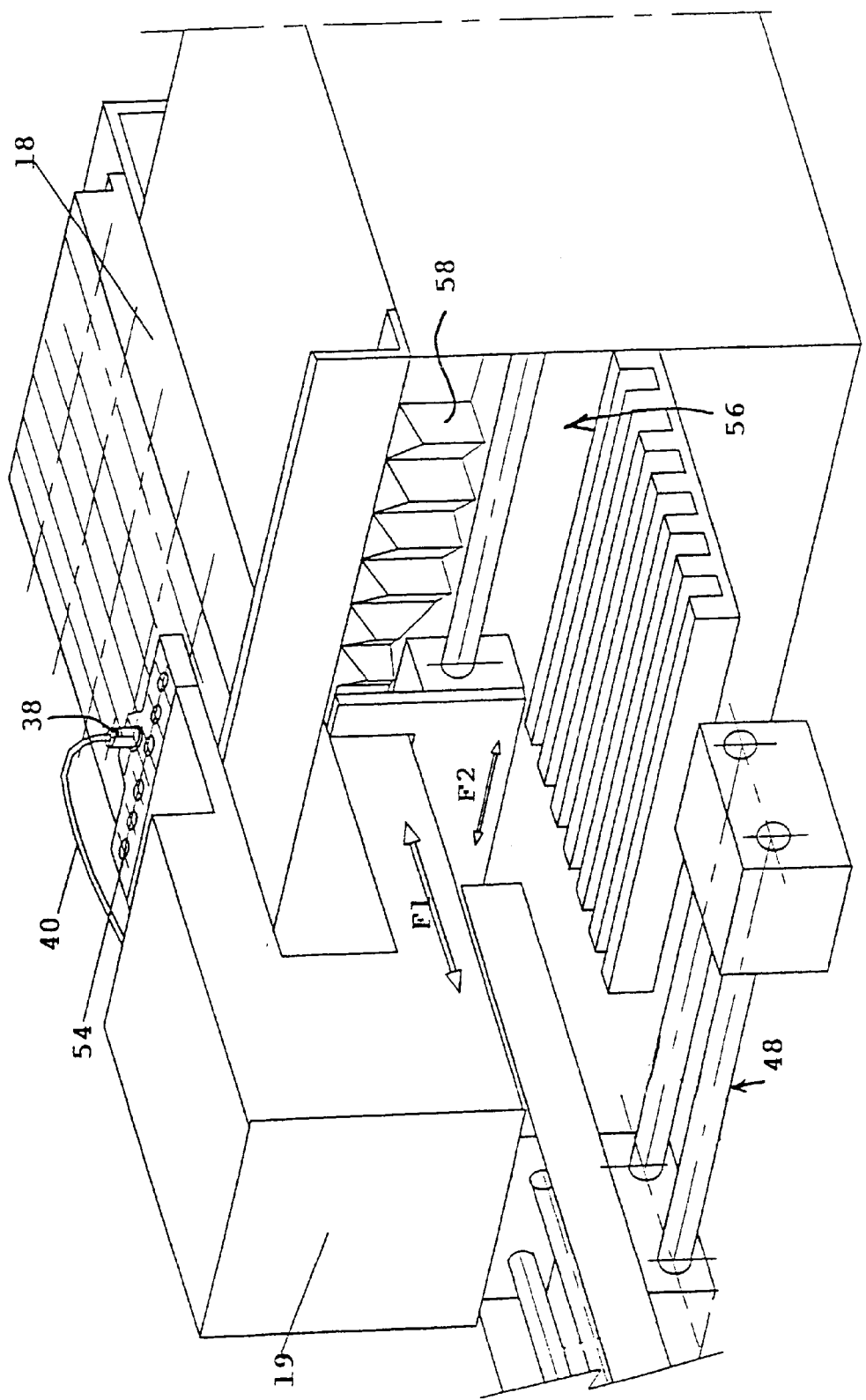
FIG. 3 represents a schematic perspective view of the analyser.

In FIGS. 1 to 3, a measuring head 10 of a laboratory chemical or biochemical reaction analyser comprises a first calorimetric analysis detector 12 and a second photometric analysis detector 14 to determine the dosing of components contained in samples, for example blood, cerebrospinal liquid, or urine. The control mechanism of the automatic analyser takes a predefined quantity of sample, and a predefined quantity of reagent, then performs mixing of these quantities in cuplets 16 of a reaction analysis plate 18 in the form of a microplate. Measurement of the evolution of the optical density by the measuring head 10 defines the concentration of the component to be dosed directly according to a pre-established methodology.

The first calorimetric analysis detector 12 uses a polychromatic colorimeter to perform biochemistry and immunology analyses. The second photometric analysis detector 14 makes use of monochromatic photometers for hemostasis reactions.

The two detectors 12, 14 are mounted on a U-shaped mobile support 19 which vertically frames the parallel opposite sides of the reaction analysis plate 18, which plate is fixed.

Description of the First Calorimetric Analysis Detector

The first colorimetric analysis detector 12 is controlled by a light source 20 arranged in fixed manner on the frame of the analyser and comprising a lamp 22 associated to an optical focussing device formed by a pair of convergent lenses 24. The light energy emitted by the lenses 24 is concentrated on one end 26 of an optic fibre 28 for transmission of the light beam to the first colorimetric analysis detector 12. The lamp 22 used can for example be of the halogen or xenon type having a broad wavelength spectrum comprised between 340 nm and 700 nm, i.e. ranging from ultraviolet to infrared, or may be of the laser type.

The other end of the optic fibre 28 is fixed in a first housing 30 at the bottom part of the mobile support 19 so as to direct the light ray coinciding with the optical axis of a predetermined cup 16 of the reaction analysis plate 18. The housing 30 contains an optical collimator 32 designed to deliver a parallel light beam, which beam passes through the transparent bottom of the cup 16 and the reaction mixture 34 and emerges via the meniscus of the mixture 34. A reference detector, 36 formed for example by a photoelectric cell, is also located in the housing 30 and operates in case of fluctuation of the light source 20 or attenuation of the light beam following deformation of the optic fibre 28.

The top part of the mobile support 19 is separated from the bottom part by the reaction analysis plate 18 and is equipped with a photodetector device 37. The latter device comprises an optical focussing system 38 situated in a second housing 39 of the mobile support 19 to collect the incident light on a second optic fibre 40 connected to a diffraction network 42 fixed onto the rear part of the mobile support 19. The diffraction network 42 enables static wavelength selection to be performed and is associated to a plurality of photodiodes 44 connected to an electronic processing circuit 46 designed to detect the incident light spectrum of the reaction mixture. Measurement of the optical density results from an equation linking the signal coming from the reference detector 36 and the output signal of each photodiode 44.

Movement of the mobile support 19 takes place along two axes (arrows F1 and F2, FIG. 3) in the horizontal plane and is performed by a drive mechanism 48 with a stepper motor 50. The measuring head 10 can thus be positioned coaxially on each cup 16 of the microplate. The optical collimator 32 illuminates the bottom of the cup 16 and the light beam passes through the medium of the mixture 34, undergoing an attenuation. The optical focussing system 38 at the top part of the measuring head 10 recovers the ray emerging from the cup 16 and conducts it to the diffraction network 42 and the photodiodes 44 to quantify this attenuation.

The optic fibre 28 fitted between the fixed light source 20 and the bottom part of the mobile support 19 is alone subjected to torsional and flectional deformation movements during positioning of the measuring head 10 and prevents any transmission of mechanical vibrations to the light source 20 and the sample to be measured on the fixed analysis plate 18.

To prevent premature wear of the optic fibre 28 due to the mechanical frictions caused by deformation, optic fibres provided with an external protective film made of highly resistant material should advantageously be used.

Passage of the light beam in the optic fibre 28 generates an attenuation which varies according to the curvature taken for a location facing a predetermined cup. This curvature can however vary for the same location between two separate measurements following a to-and-fro movement of the mobile support 19. To prevent any measurement error arising from these variations, the photoelectric cell of the reference detector 36 located in the housing 30 quantifies the cumulated variation of the attenuation of the optic fibre 28 and any deviation of the intensity of the light source 20 which may occur. The electronic circuit 46 takes the measurement supplied by the reference detector 36 into account and compensates the measurements delivered by the photodiodes 44.

A biochemical or immunological reaction undergoes a relatively slow optical density evolution, and measurement with a frequency of every thirty seconds is sufficient to obtain a reliable result. The mobile support 19 can then scan the other cups 16 before returning to make a measurement on the current cup.

Description of the Second Photometric Analysis Detector

The second photometric analysis detector 14 is used for a hemostasis reaction in which the reaction mixture in the cup 16a is formed by a sample of human plasma and a specific reagent triggering a coagulation effect.

Coagulation is accompanied by a variation of the opacity of the mixture in the cup 16a, and the role of the photometric analysis detector 14 is to determine, by means of a specific algorithm, the time required to obtain coagulation of the reaction mixture.

When hemostatic analysis is performed, the variation of the opacity of the mixture varies very quickly at the moment coagulation takes place, and the timing precision must be to within a tenth of a second. The coagulation reaction is supervised continuously until the blood clot forms.

The mobile support 19 of the measuring head 10 is provided at its bottom part with a row of six light-emitting diodes 52 for emission of a monochromatic light, each light-emitting diode being associated to a collimator. The light beam emitted by each diode 52 passes through the corresponding reaction cup 16a following a vertical path. A series of six photodiodes 54 is arranged facing the diodes 52 on the upper part of the measuring head 10 and intercepts the ray emerging from each cup 16a for an opacity measurement. The optical axis of each light-emitting diode 52 corresponds to that of a photodiode 54 and to the main axis of the cup 16a. The energy supplied by the light-emitting diodes 52 is sufficient to perform chronometric hemostatic analyses.

The six sensors of the second photometric analysis detector 14 enable monitoring of several hemostatic reactions to be performed in parallel in the six cups 16a.

The present invention enables two different measurement systems arranged on the mobile support 19 to be integrated in the measuring head 10. This arrangement enables analyses to be initiated in the fields of biochemistry, immunology, or hemostasis with the same sample and reagent storage supports, the same sampling equipment, and the same reaction cups.

A reaction in the biochemistry, immunology and hemostasis fields has to take place under conditions as close as possible to the natural environment where it normally takes place. The reagents used are moreover sensitive to any temperature variation, especially for the enzyme type. The analysis plate 18 is kept at constant temperature throughout performance of the analysis. More often than not, this temperature is fixed at 37° C. to coincide with the temperature of the human body.

With reference to FIG. 3, heating of the reaction analysis plate 18 to the required temperature is performed by forced convection of hot air at a temperature close to 37° C. To limit heat losses when the mobile support 19 is moved, a thermal enclosure 56 is arranged under the analysis plate 18. The enclosure 56 is formed by a flexible material with an accordion wall 58 securedly affixed to the mobile support 19 and enabling the analysis plate 18 to be heated to the required temperature with minimum heat loss, while allowing full freedom of movement of the mobile support 19 under the analysis plate 18. The volume of the enclosure 56 is confined by four side walls and a bottom wall, the top wall being formed by the bottom face of the analysis plate 18. This plate can be heated by forced convection by means of a fan (not represented) and an electronic circuit controlled by temperature sensors performs thermostatic regulation.

The deformable rear wall fixedly secured to the mobile support 19 is formed by a flexible sheet arranged in the form of an accordion and in addition fixed against the side walls of the enclosure 56. Movement of the mobile support 19 deforms the flexible accordion wall 58, while at the same time ensuring that the thermostatic enclosure 56 is kept tightly sealed.

Figure 4:
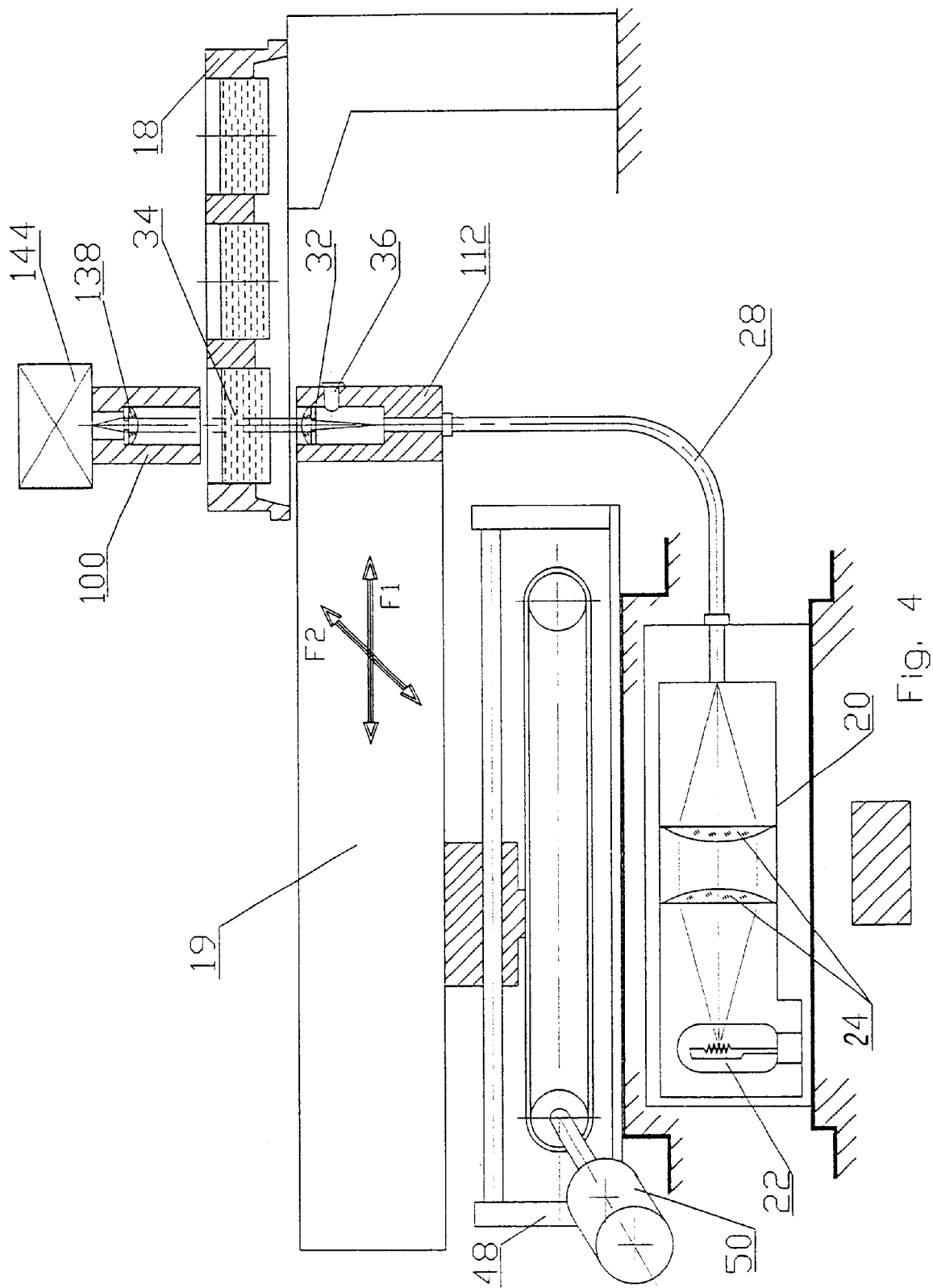
FIG. 4 is a similar view to FIG. 1 of an alternative embodiment using a measuring head by colorimetry.

FIG. 4 shows an alternative embodiment of a measuring head 100 making use of a single calorimetric analysis detector 112. All the parts identical to those of the device of FIG. 1 will not be described and will bear the same reference numbers in FIG. 4. The receiver photodiodes 144 are arranged directly up-line from the optical focussing system 138 with respect to the direction of propagation of the light beam. The optic fibre 40 is then eliminated.

The present invention naturally extends to encompass other chemical reaction analyses, and the measuring method by mobile optic fibre 28 of the first calorimetric analysis detector 12 can apply to any characterization of a solid, liquid or gas medium in transmission, reflection, refraction, diffraction, or diffusion using a natural, polarized, or coherent light in a monochromatic or polychromatic mode.

What is claimed is:

1. An optical measuring head for an automatic laboratory chemical or biochemical reaction analyser designed to determine the dosing of components contained in samples after mixing with reagents in cups (16, 16a) of a reaction analysis plate (18), said measuring head comprising:
   a first colorimetric analysis detector (12, 122) controlled by a light source (20) associated to an optic fibre (28) for transmission of the light beam to one of the sides of the reaction analysis plate (18), coinciding with the optic axis of a predetermined cup, which cup is made of transparent material,
   means for focussing the light beam when the latter passes through the reaction mixture (34) in said cup (16),
   a photodetector device (37) arranged on the opposite side of the analysis plate (18) to collect the light beam emerging from the cup (16) after this beam has been subjected to an attenuation,
   and an electronic processing circuit (46) for processing the signal delivered by the photodetector device (37) to determine the light spectrum or the optical density of the reaction mixture (34),
   characterized in that:
   the light source (20) and the reaction analysis plate (18) are fixed,
   the measuring head (10, 100) comprises a U-shaped mobile support (19) framing the parallel opposite sides of the reaction analysis plate (18), and a drive mechanism (48) of said mobile support to bring the first calorimetric analysis detector (12, 112) to face a predetermined cup,
   the optic fibre (28) has one end secured to the fixed light source (20) and an opposite end arranged in a first housing (30) of the mobile support (19).

2. An analyser comprising an optical measuring head according to claim 1, a thermal enclosure designed to receive said analysis plate, characterized in that the bottom face of the analysis plate (18) is kept at a preset temperature by a thermostatic control.

3. The optical measuring head according to claim 1, characterized in that the first housing (30) of the mobile support contains an optical collimator (32) to deliver a parallel light beam and a reference photoelectric detector (36) connected to the electronic circuit (46) to compensate the light flux variations when deformation of the optic fibre occurs (28).

4. The optical measuring head according to claim 3, characterized in that the measuring head (10) is equipped with a second photometric analysis detector (14) arranged on the mobile support (19) to perform an opacimetry measurement.

5. An analyser comprising an optical measuring head according to claim 3, and a thermal enclosure designed to receive said analysis plate, characterized in that the bottom face of the analysis plate (18) is kept at a preset temperature by a thermostatic control.

6. The optical measuring head according to claim 3, characterized in that the mobile support (19) comprises a second housing (39) located opposite the first housing (30) and containing an optical focussing system (38) optically linked with the photodetector device (37).

7. The optical measuring head according to claim 6, characterized in that the measuring head (10) is equipped with a second photometric analysis detector (14) arranged on the mobile support (19) to perform an opacimetry measurement.

8. An analyser comprising an optical measuring head according to claim 6, and a thermal enclosure designed to receive said analysis plate, characterized in that the bottom face of the analysis plate (18) is kept at a preset temperature by a thermostatic control.

9. The optical measuring head according to claim 1, characterized in that the optical focussing system (38) is connected to a diffraction network (42) for static wavelength selection.

10. The optical measuring head according to claim 9, characterized in that the measuring head (10) is equipped with a second photometric analysis detector (14) arranged on the mobile support (19) to perform an opacimetry measurement.

11. An analyser comprising an optical measuring head according to claim 9, and a thermal enclosure designed to receive said analysis plate, characterized in that the bottom face of the analysis plate (18) is kept at a preset temperature by a thermostatic control.

12. The optical measuring head according to claim 9, characterized in that the optical focussing system (38) is connected to the diffraction network (42) by means of a second optic fibre (40).

13. The optical measuring head according to claim 12, characterized in that the measuring head (10) is equipped with a second photometric analysis detector (14) arranged on the mobile support (19) to perform an opacimetry measurement.

14. An analyser comprising an optical measuring head according to claim 12, and a thermal enclosure designed to receive said analysis plate, characterized in that the bottom face of the analysis plate (18) is kept at a preset temperature by a thermostatic control.

15. An optical measuring head, in particular for an automatic laboratory chemical or biochemical reaction analyser designed to determine the dosing of components contained in samples after mixing with reagents in cups (16, 16a) of a reaction analysis plate (18), said measuring head comprising:

a first colorimetric analysis detector (12, 122) controlled by a light source (20) associated to an optic fibre (28) for transmission of the light beam to one of the sides of the reaction analysis plate (18), coinciding with the optic axis of a predetermined cup, which cup is made of transparent material;

means for focussing the light beam when the latter passes through the reaction mixture (34) in said cup (16);

a photodetector device (37) arranged on the opposite side of the analysis plate (18) to collect the light beam emerging from the cup (16) after this beam has been subjected to an attenuation; and an electronic processing circuit (46) for processing the signal delivered by the photodetector device (37) to determine the light spectrum or the optical density of the reaction mixture (34), wherein the light source (20) and the reaction analysis plate (18) are fixed, the measuring head (10, 100) is mounted on a U-shaped mobile support (19) framing the parallel opposite sides of the reaction analysis plate (18) and able to be moved by a drive mechanism (48) to bring the first colorimetric analysis detector (12, 112) to face a predetermined cup, the optic fibre (28) has one end secured to the fixed light source (20) and an opposite end arranged in a first housing (30) of the mobile support (19), and the measuring head (10) is equipped with a second photometric analysis detector (14) arranged on the mobile support (19) to perform an opacimetry measurement.

16. An analyser comprising an optical measuring head according to claim 15, and a thermal enclosure designed to receive said analysis plate, characterized in that the bottom face of the analysis plate (18) is kept at a preset temperature by a thermostatic control.

17. The optical measuring head according to claim 15, characterized in that the second photometric analysis detector (14) comprises at least one light-emitting diode (52) for emission of a monochromatic light, operating in conjunction with a receiver photodiode (54) on the opposite side of the mobile support (19).

18. An analyser comprising an optical measuring head according to claim 17, and a thermal enclosure designed to receive said analysis plate, characterized in that the bottom face of the analysis plate (18) is kept at a preset temperature by a thermostatic control.

19. An optical measuring head, in particular for an automatic laboratory chemical or biochemical reaction analyser designed to determine the dosing of components contained in samples after mixing with reagents in cups (16, 16a) of a reaction analysis plate (18), said measuring head comprising:

a first colorimetric analysis detector (12, 122) controlled by a light source (20) associated to an optic fibre (28) for transmission of the light beam to one of the sides of the reaction analysis plate (18), coinciding with the optic axis of a predetermined cup, which cup is made of transparent material;

means for focussing the light beam when the latter passes through the reaction mixture (34) in said cup (16);

a photodetector device (37) arranged on the opposite side of the analysis plate (18) to collect the light beam emerging from the cup (16) after this beam has been subjected to an attenuation; and an electronic processing circuit (46) for processing the signal delivered by the photodetector device (37) to determine the light spectrum or the optical density of the reaction mixture (34), wherein the light source (20) and the reaction analysis plate (18) are fixed, the measuring head (10, 100) is mounted on a U-shaped mobile support (19) framing the parallel opposite sides of the reaction analysis plate (18) and able to be moved by a drive mechanism (48) to bring the first calorimetric analysis detector (12, 112) to face a predetermined cup, the optic fibre (28) has one end secured to the fixed light source (20) and an opposite end arranged in a first housing (30) of the mobile support (19), the bottom face of the analysis plate (18) is confined in a closed enclosure (56) kept at a preset temperature by a thermostatic control and the enclosure (56) is provided with a deformable flexible wall (58) allowing the mobile support (19) to move under the analysis plate (18).

20. An optical measuring head, in particular for an automatic laboratory chemical or biochemical reaction analyser designed to determine the dosing of components contained in samples after mixing with reagents in cups (16, 16a) of a reaction analysis plate (18), said measuring head comprising:

a first colorimetric analysis detector (12, 122) controlled by a light source (20) associated to an optic fibre (28) for transmission of the light beam to one of the sides of the reaction analysis plate (18), coinciding with the optic axis of a predetermined cup, which cup is made of transparent material;

means for focussing the light beam when the latter passes through the reaction mixture (34) in said cup (16);

a photodetector device (37) arranged on the opposite side of the analysis plate (18) to collect the light beam emerging from the cup (16) after this beam has been subjected to an attenuation a second sensor having a row of a plurality of light-emitting diodes (52) and associated with receiver diodes; and an electronic processing circuit (46) for processing the signal delivered by the photodetector device (37) to determine the light spectrum or the optical density of the reaction mixture (34), wherein the light source (20) and the reaction analysis plate (18) are fixed, the measuring head (10, 100) is mounted on a U-shaped mobile support (19) framing the parallel opposite sides of the reaction analysis plate (18) and able to be moved by a drive mechanism (48) to bring the first colorimetric analysis detector (12, 112) to face a predetermined cup, the optic fibre (28) has one end secured to the fixed light source (20) and an opposite end arranged in a first housing (30) of the mobile support (19), and the measuring head (10) is equipped with a second photometric analysis detector (14) arranged on the mobile support (19) to perform an opacimetry measurement.

* * * * *